US011730832B2

(12) United States Patent
Langseth-Manrique et al.

(10) Patent No.: US 11,730,832 B2
(45) Date of Patent: *Aug. 22, 2023

(54) PLASTIC CONTAINERS

(71) Applicant: GE Healthcare AS, Oslo (NO)

(72) Inventors: Karina Martha Langseth-Manrique, Oslo (NO); Arne Wang Aabye, Oslo (NO); Harald Laugen, Oslo (NO); Eva Krog Tamnes, Oslo (NO); Borge Mathisen, Oslo (NO)

(73) Assignee: GE HEALTHCARE AS, Oslo (NO)

( * ) Notice: Subject to any disclaimer, the term of this patent is extended or adjusted under 35 U.S.C. 154(b) by 241 days.

This patent is subject to a terminal disclaimer.

(21) Appl. No.: 17/079,724

(22) Filed: Oct. 26, 2020

(65) Prior Publication Data
US 2021/0069355 A1 Mar. 11, 2021

Related U.S. Application Data

(62) Division of application No. 15/877,095, filed on Jan. 22, 2018, now Pat. No. 10,842,888.

(60) Provisional application No. 62/448,698, filed on Jan. 20, 2017.

(30) Foreign Application Priority Data

Feb. 28, 2017 (GB) .................................... 1703227

(51) Int. Cl.
| A61K 49/10 | (2006.01) |
| B65B 3/00 | (2006.01) |
| A61J 1/10 | (2006.01) |
| A61J 1/05 | (2006.01) |
| A61B 5/055 | (2006.01) |

(52) U.S. Cl.
CPC ............. *A61K 49/108* (2013.01); *A61J 1/05* (2013.01); *B65B 3/003* (2013.01); *A61B 5/055* (2013.01); *A61J 1/10* (2013.01)

(58) Field of Classification Search
CPC ........... A61K 49/108; A61B 5/055; A61J 1/10
See application file for complete search history.

(56) References Cited

U.S. PATENT DOCUMENTS

| 5,450,847 A | 9/1995 | Kaempfe et al. |
| 5,772,651 A | 6/1998 | Haen et al. |
| 6,065,270 A | 5/2000 | Reinhard et al. |
| 2010/0016714 A1 | 1/2010 | Nagata et al. |
| 2014/0065076 A1 | 3/2014 | Hollander et al. |

FOREIGN PATENT DOCUMENTS

| JP | H069435 A | 1/1994 |
| JP | H06299681 A | 10/1994 |
| JP | H08155007 A | 6/1996 |
| JP | 2013053160 A | 3/2013 |
| JP | 2015528351 A | 9/2015 |
| WO | 9512482 A1 | 5/1995 |
| WO | 2014036402 A1 | 6/2014 |
| WO | 2016083600 A1 | 6/2016 |

OTHER PUBLICATIONS

Office Action received in Japanese Application No. 2019539162 dated Aug. 3, 2021, with translation, 6 pages.
Great Britain Search Report from GB Appl. No. GB1703227.7, dated Nov. 27, 2017.
Guerbel Laboratories Ltd., Package Leaflet Information for the User for DOTAREM 0.5mml/ml Solution for Injection, 6 pages, http://www.mhra.gov .uk/home/groups/spcpi l/docu ments/spcpi l/con 150787264 7871.pdf.
International Search Report and the Written Opinion of the International Searching Authority, or the Declaration from International Appl. No. PCT/EP2018/051480, dated Apr. 16, 2018.
Mallinckrodt Inc., OpliMark (Gadoversetamide Injection), http:l/www.accessdata.fda.gov/drugsalfda.docs/label /2010/020976s016lbl.pdf, 32 pages.
MHRA Public Assessment Report, "MultiHance 529mg/ml Solution for Injection in Pre-Filled Syringe," "Container Closure System," and "Preclinical Aspects," 2 pages, http://www.mhra.gov.uk/home/groups/par/documents/websiteresources/atleastcon0, 148 70.
Micard el al., "Stability and Sterility of Meglumine Gadolerale Injection Repackaged in Plastic Syringes," International Journal of Pharmaceutics, vol. 212, No. 1, 2001, pp. 93-99.
S. Micard et al., Stability and sterility of meglumine gadoterate injection repackaged in plastic syringes, Intl. J. Pharmaceutics, 212, 93-99. (Year: 2001).
Office Action received in Japanese Application No. 2019-539162 dated Apr. 4, 2023, with translation, 10 pages.

*Primary Examiner* — Michael G. Hartley
*Assistant Examiner* — Jagadishwar R Samala
(74) *Attorney, Agent, or Firm* — Jeff B. Vockrodt; Culhane Meadows PLLC

(57) ABSTRACT

The present invention provides a method for the commercial presentation of a solution of gadolinium-DOTA that provides certain advantages over the known methods.

15 Claims, 3 Drawing Sheets

PLASTIC CONTAINERS

TECHNICAL FIELD OF THE INVENTION

The present invention relates to in vivo medical imaging and especially to magnetic resonance imaging (MRI). More particularly, the present invention relates to a convenient commercial presentation of a solution of an MRI contrast agent.

DESCRIPTION OF RELATED ART

Metal complexes of lanthanide metals, especially gadolinium, are of interest as MRI contrast agents in the field of in vivo medical imaging. MRI contrast agents based on metal complexes of gadolinium have been reviewed extensively (see e.g. Zhang et al. 2005 Curr Med Chem; 12: 751-778 and Aime et al. 2005 Adv Inorg Chem; 57: 173-237).

Gadoteric acid meglumine is a product marketed by Guerbet as Dotarem. The product is commercially supplied in glass vials and glass pre-filled syringes (https://www.accessdata.fda.gov/drugsatfda_docs/label/2017/204781s001lbl.pdf). The prescribing information instructs that when Dotarem® is to be injected using plastic disposable syringes, the contrast medium should be drawn into the syringe and used immediately.

Micard et al. (2001 Int J Pharmaceutics; 212: 93-99) discusses repackaging of Dotarem® into single-use polypropylene syringes and notes that the solution is stable and sterile according to European Pharmacopoeia up to 90 days in the dark at either 4° C. or at room temperature. However, established guidelines advise that a pharmaceutical product drawn into a single-use syringe should be used within 24 hours (http://www.ema.europa.eu/docs/en_GB/document_library/Scientific_guideline/2009/09/WC500003476.pdf).

SUMMARY OF THE INVENTION

In a first aspect the present invention provides a method for providing a solution comprising gadolinium-DOTA wherein said method comprises:
  (i) manufacturing a commercial batch of said solution; and,
  (ii) dispensing said solution into plastic containers.

In a second aspect the present invention provides a magnetic resonance imaging (MRI) method comprising:
  (a) providing a plastic container containing a solution comprising gadolinium-DOTA;
  (b) administering an imaging effective amount of said solution to a subject; and,
  (c) performing MRI on said subject.

Up until the present invention glass containers have been selected for product presentations of gadolinium-DOTA, perhaps due to their relatively low susceptibility to ingress of oxygen and moisture and to chemical leaching as compared with plastic containers. However, it has been demonstrated herein that plastic containers permit long-term storage of gadolinium-DOTA without any detrimental effect on product quality due to oxygen or moisture ingress or chemical leaching. Furthermore, the present invention overcomes problems presented by glass containers including their relative ease of breakage, the need to dispose in special containers, their relatively heavy weight and high eco-impact.

DETAILED DESCRIPTION OF THE PREFERRED EMBODIMENTS

Figure 1:
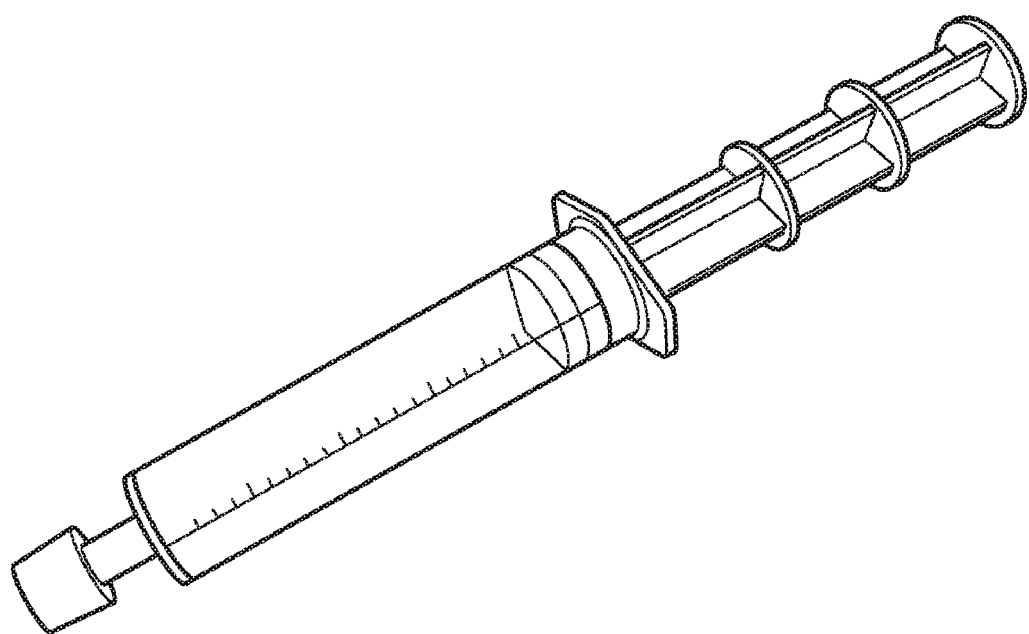
FIG. 1 shows a non-limiting example of a syringe suitable for use in the present invention.

To more clearly and concisely describe and point out the subject matter of the claimed invention, definitions are provided hereinbelow for specific terms used throughout the present specification and claims. Any exemplification of specific terms herein should be considered as a non-limiting example.

The terms "comprising" or "comprises" have their conventional meaning throughout this application and imply that the agent or composition must have the essential features or components listed, but that others may be present in addition. The term 'comprising' includes as a preferred subset "consisting essentially of" which means that the composition has the components listed without other features or components being present.

The term "a solution comprising gadolinium-DOTA" can encompass a solution of gadolinium-DOTA (also can be referred to as "gadoteric acid") prior to formulation as a contrast agent or to the actual formulated contrast agent ready for use. The term "contrast agent" has its conventional meaning in the field of in vivo medical imaging, and refers to an agent in a form suitable for mammalian administration, which assists in providing clearer images in the region or organ of interest than could be obtained by imaging a subject to whom no contrast agent has been administered. A contrast agent comprising gadolinium-DOTA is an "RI contrast agent", suitable for mammalian administration, which shortens the T1 and/or T2 relaxation time of the relevant nuclei (e.g. 1H for 1H NMR) in the region of interest for imaging within a subject.

In one embodiment of the method of the invention said gadolinium-DOTA is the meglumine salt of gadolinium-DOTA, also commonly referred to as Gd-DOTA meglumine or gadoterate meglumine.

In one embodiment the solution comprising gadolinium-DOTA further comprises a mol/mol amount of free DOTA between 0.002% and 0.4%, in another embodiment between 0.02 and 0.3% of free DOTA, in another embodiment between 0.025 and 0.25 mol/mol % of free DOTA.

The macrocyclic chelator DOTA and its metal complexes in biomedical imaging have been described by Stasiuk and Long (2013 Chem Comm; 49: 2732-2746) and has the following structure:

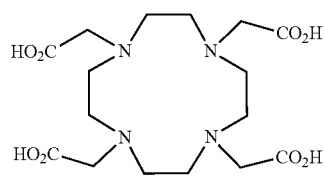 [SMILES: O=C(O)CN1CCN(CC(=O)O)CCN(CC(=O)O)CCN(CC(=O)O)CC1]

DOTA is commercially available from a range of suppliers and can also be synthesised by the method of Desreux (1980 Inorg Chem; 19: 1319-1324). Further details on macrocyclic chelator syntheses are given by Kotel et al. (Chapter 3 pages 83-155 in "The Chemistry of Contrast Agents in Medical Magnetic Resonance Imaging; Wiley 2$^{nd}$ Edition 2013: A. Merbach, L. Helm & E. Toth, Eds).

Meglumine (N-methylglucamine) is commercially available from a range of suppliers. Pharmaceutical grade material is generally used.

The complexation of lanthanides such as gadolinium by macrocyclic chelators is a multistep process that results in a thermodynamically stable metal complex. Non-limiting examples of gadolinium-DOTA solutions as well as methods to prepare gadolinium-DOTA and its meglumine salt are described in WO 2009/103744, WO 2016/083597, WO 2016/083600 and WO 2016/083605, the contents of which are hereby incorporated by reference. US 2012/0082624 A1 discloses a similar process to WO 2009/103744, except that the pharmaceutical formulation is obtained in powder form.

By the phrase "in a form suitable for mammalian administration" is meant a composition which is sterile, pyrogen-free, lacks compounds which produce toxic or adverse effects, and is formulated at a biocompatible pH (approximately pH 4.0 to 10.5) in a biocompatible carrier. Such compositions lack particulates which could risk causing emboli in vivo, and are formulated so that precipitation does not occur on contact with biological fluids (e.g. blood). Such compositions also contain only biologically compatible excipients, and are preferably isotonic.

By the term "biocompatible carrier" is meant a fluid, especially a liquid, such that the composition is physiologically tolerable, i.e. can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is isotonic); an aqueous buffer solution comprising a biocompatible buffering agent (e.g. phosphate buffer); an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like). Preferably the biocompatible carrier is pyrogen-free water for injection (WFI), isotonic saline or phosphate buffer.

Production of the solution comprising gadolinium-DOTA is suitably carried out under aseptic manufacture conditions. The phrase "aseptic manufacture" refers to carrying out the relevant process steps under aseptic manufacture, i.e. apyrogenic conditions, e.g. in a clean-room environment, including terminal sterilisation. The term "sterilisation" takes its conventional meaning, and refers to a process of destruction of micro-organisms, to obtain a sterile, pyrogen-free composition. The phrase "terminal sterilisation" has its conventional meaning, and refers to carrying out the preceding steps to GMP (Good Manufacturing Practice), but carrying out the sterilisation step as late as possible in the overall process. The components and reagents can be sterilised by methods known in the art, including: sterile filtration, terminal sterilisation using e.g. gamma-irradiation, autoclaving, dry heat or chemical treatment (e.g. with ethylene oxide) or combinations thereof. The term "autoclaving" has its' conventional meaning, and refers to one particular method of sterilisation which uses superheated steam to sterilise. Autoclaving and other sterilisation methods are described in *Achieving Sterility in Medical and Pharmaceutical Products*, N. Halls (CRC Press, 1994).

The term "commercial batch" refers to a relatively large quantity of the solution comprising gadolinium-DOTA to fulfil demand for commercial product offerings comprising said solution. In one embodiment a commercial batch may be regarded as a batch having a volume of around 400 L or greater, up to around 1500 L. For example, in certain embodiments said commercial batch has a volume around 600 L or greater, around 700 L or greater, around 800 L or greater, around 900 L or greater, around 1000 L or greater, or between 1000-1500 L, for example 1400 L.

The term "plastic containers" in the context of the present invention is intended to refer to containers made of pharmaceutical grade plastic suitable for the safe and efficient storage, transport and handling of the gadolinium-DOTA solution. Such containers can be readily obtained commercially. In certain embodiments of the invention said plastic containers are made from pharmaceutical-grade polypropylene. In other embodiments of the invention said plastic containers are made from pharmaceutical-grade cyclic olefin. Examples of particular plastic containers suitable for the present invention include plastic syringes, plastic containers and plastic bags. Where the plastic container is a syringe or a bottle it is suitable for containing one or more imaging effective doses of the solution where the solution is the final formulated solution of gadolinium DOTA suitable for use as an MRI agent.

Non-limiting examples of suitable syringes include those having a 10 mL, 15 mL or 20 mL volume. A non-limiting example of a syringe suitable for the present invention is illustrated in FIG. 1. The following characteristics are present in certain embodiments of plastic syringes suitable for the present invention:

Durable, medical-grade pharmaceutical polymer construction
Dispose in regular waste disposal
Are fully re-cyclable
Cost saving
Lighter weight In one embodiment said syringe is made from pharmaceutical-grade cyclic olefin. Cyclic olefin has good transparency, which facilitates visually verifying the contents.

Figure 2:
FIG. 2 shows non-limiting examples of bottles suitable for use in the present invention.
Figure 3A:
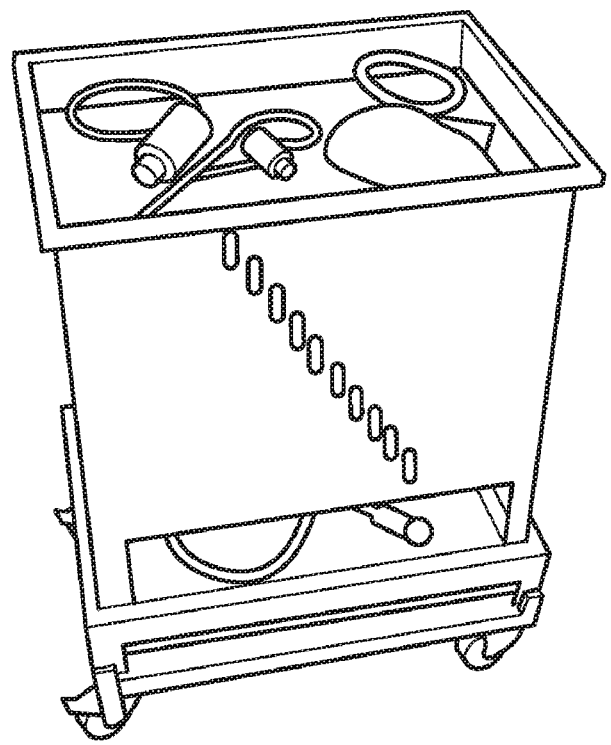
FIG. 3A shows a non-limiting example of a bag suitable for use in the present invention (from Sartorius Stedim).
Figure 3B:
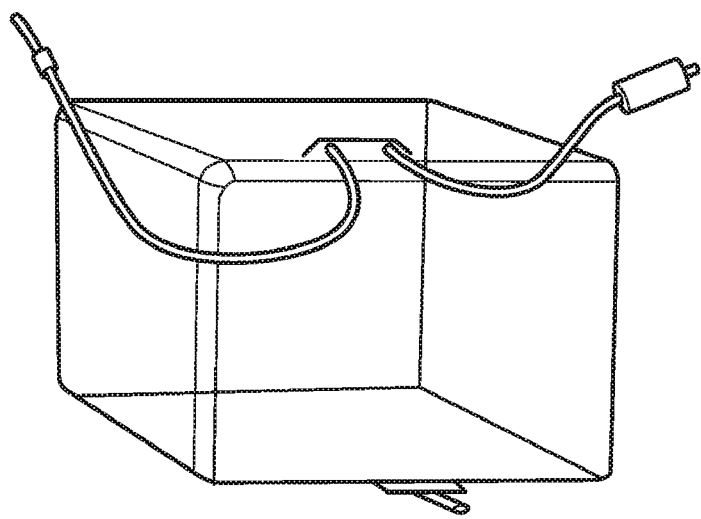
FIG. 3B shows a non-limiting example of a bag suitable for use in the present invention (from Sartorius Stedim).

Non-limiting example of suitable bottles are those having volumes between 50-500 mL, e.g. 50 mL, 100 mL, 150 mL, 500 mL or 1000 mL. In one embodiment said bottle can be of the type described in WO 00/03920. In certain embodiments said bottle may be of a type as described in any of U.S. Pat. No. 6,659,296, WO2013041593, U.S. Pat. No. 9,815,601, EP 2790636 B1, U.S. Pat. No. 9,682,015, WO2014106002 and WO2016014406. In one embodiment said bottle can be the Pluspak™ available from GE Healthcare of the type illustrated in FIG. 2. Pluspak™ is a polypropylene based bottle having the following characteristics:

Durable, medical-grade pharmaceutical polymer construction
Easy twist-off cap without metal Latex-free stopper
Latex-free stopper
Dispose in regular waste disposal
Fully re-cyclable
Cost saving
Compact size, 75% lighter weight (100 ml)
Average of 41% lower eco-impact than glass during whole lifecycle (vs. GEHC glass bottles)

Where the plastic container is a bag it is in one embodiment a flexible plastic bag suitable for the transport and storage of the gadolinium-DOTA solution. Suitable plastic bags are commercially available and non-limiting examples of these are illustrated in FIG. 3. In one embodiment the plastic bag of the invention has a 50-1000 L volume.

Particular properties of a suitable bag include:
Pharmacopoeia compliance.
Enables transport and storage of the gadolinium-DOTA solution.
Is more Eco-friendly vs. steel drums.
The bags are flexible with respect to filling volumes.

In certain embodiments of the invention said method further comprises the step (iii) of storing said solution dispensed into said plastic containers. The term "storing" takes its conventional meaning of placing or leaving in a suitably secure location for preservation with the intention to use at a later date. In one embodiment of the method of the invention said storing is for more than 90 days, for example for up to 36 months. In one embodiment of the method of the invention said storing is at temperatures up to 30° C. The present inventors have demonstrated that storing is possible over a wide range of temperatures and for a long shelf life without any impact on the quality of the gadolinium-DOTA solution.

Both oxygen content and free Gd were tested by for up to 24 months for the drug product stored at both 25° C./40% RH (RH=relative humidity) and 30° C./75% RH and up to 6 months at 40° C./75% RH and 40° C./20% RH. Furthermore, the product was tested for oxygen and free Gd after both confirmatory photostability testing according to ICH Q1B (which may be viewed at this link: http://www.ich.org/fileadmin/Public_Web_Site/ICH_Products/Guidelines/Quality/Q1B/Step4/Q1B_Guideline.pdf) and temperature cycling from −20° C. to 60° C. All results show that free Gd has not been detected indicating stability of the product under the various storage conditions. ICH Q1E guideline (which may be viewed at this link: http://www.ich.org/fileadmin/Public_Web_Site/ICH_Products/Guidelines/Quality/Q1E/Step4/Q1E_Guideline.pdf) allows extrapolation up to a 30 months shelf life at the long term storage condition of 25° C./40% RH. Therefore, the results obtained by the present inventors demonstrate that gadoterate meglumine solution can be effectively stored in semi-permeable containers such as polymer PFS and PP bottles during long term storage at 25° C./40% RH up to 30 months. This is despite some of the harsh conditions to which the product was exposed and the fact that these containers permit ingress of oxygen resulting in raised oxygen levels in the containers.

In certain embodiments of the method of the invention said dispensing includes carrying out an overfill to counteract any water loss from plastic containers over time in order to maintain product quality. In one embodiment said overfill is 1-5% of the final desired volume.

In certain embodiments of the method of the invention nitrogen is not used as an excipient in the plastic container headspace. The present inventors have demonstrated that oxygen in the headspace of the plastic containers does not have a material impact on the quality of the product.

The term "magnetic resonance imaging" herein takes its ordinary meaning in the art, that is a form of medical imaging that measures the response of the atomic nuclei of body tissues to high-frequency radio waves when placed in a strong magnetic field, and that produces images of the internal organs.

The term "an imaging effective amount" refers to an amount of the gadolinium-DOTA active agent sufficient to produce useful images using MRI following administration to a subject. For adult and paediatric patients (2 years and older), the recommended dose of the gadolinium-DOTA product Dotarem® is 0.2 mL/kg (0.1 mmol/kg) body weight administered as an intravenous bolus injection, manually or by power injector, at a flow rate of approximately 2 mL/second for adults and 1-2 mL/second for pediatric patients. Additional information can be found at http://www.guerbet-us.com/products/dotarem.html.

By the term "subject" is meant a mammal in vivo, preferably the intact mammalian body in vivo, and more preferably a living human subject.

As with other in vivo imaging agents, the contrast agent is designed to have minimal pharmacological effect on the mammalian subject to be imaged. Preferably, the contrast agent can be administered to the mammalian body in a minimally invasive manner, i.e. without a substantial health risk to the subject when carried out under professional medical expertise. Such minimally invasive administration is preferably intravenous administration into a peripheral vein of said subject, without the need for local or general anaesthetic.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties, as if they were individually incorporated.

BRIEF DESCRIPTION OF THE EXAMPLES

Example 1 describes preparation and storage of a gadoteric acid solution and measurements of stability over time and under different storage conditions.

LIST OF ABBREVIATIONS USED IN THE EXAMPLES

GC-TCD gas chromatography-thermal conductivity detector
ICH International Conference on Harmonisation
ND not detected
PFS polymer pre-filled syringes
PP polypropylene
RH relative humidity Example 1: Stability of Solution Comprising Gadolinium-DOTA in Plastic Containers Under Various Storage Conditions A gadoteric acid solution suitable for injection (referred to as Drug Product below) was prepared in three commercial scale 400 L batches. Each batch was filled into glass, PFS and PP bottles and autoclaved prior to storage. In order to cover climatic zone I, II and IV Drug Product samples were stored long term up 24 months at both 25° C./40% RH and 30° C./75% RH and at the accelerated storage conditions of both 40° C./75% RH and 40° C./20% RH up to 6 months. Furthermore, confirmatory photostability testing according to ICH Q1B has been performed and temperature cycling from −20° C. to 60° C. has been performed.

PFS data is detailed below to demonstrate both Free Gd and level of oxygen content. Satisfactory results below detection limit for Free Gd (limit of detection=NMT 3 µL/mL) were also obtained for PP bottles up to 24 months at 25° C./40% RH and 30° C./75% RH and for bags up to 6 months at 25° C./40% RH, 30° C./75% RH and 40° C./20% RH. All results for the Drug Product met specification for all containers mentioned above.

Measured oxygen content increased up to 20% during storage long term storage at 25° C./40% RH and 30° C./75% RH, the same trend is seen for samples stored at the accelerated storage condition of 40° C./75% RH and 40° C./20% RH up to 6 months. The increase in oxygen content was not shown to impact the stability of the drug product throughout shelf life. No free Gd was detected during stability testing. See Table 1 below for a summary of the various batches of product filled in PFS stored and tested and an index to the results for each batch.

TABLE 1

Index to stability result tables for 20 mL syringes with fill volumes 10, 15 and 20 mL

| Fill volume (mL) | Batch number | Storage condition | | | | Results presented in |
|---|---|---|---|---|---|---|
| | | ° C. | % RH | Position | Light | |
| 10 | 1 | 25 | 40 | On-side | Dark | Table 2 |
| | 1 | 30 | 75 | On-side | Dark | Table 3 |
| | 1 | 40 | 20 | On-side | Dark | Table 4 |
| | 1 | 40 | 75 | On-side | Dark | Table 5 |
| | 1 | 25 | Ambient | On-side | Light | Table 6 |
| 15 | 2 | 25 | 40 | On-side | Dark | Table 7 |
| | 2 | 30 | 75 | On-side | Dark | Table 8 |
| | 2 | 40 | 20 | On-side | Dark | Table 9 |
| | 2 | 40 | 75 | On-side | Dark | Table 10 |
| 10 | 1 | −20 to 60 | Ambient | On-side | Dark | Table 11 |
| 20 | 3 | 25 | 40 | On-side | Dark | Table 12 |
| | 3 | 30 | 75 | On-side | Dark | Table 13 |
| | 3 | 40 | 20 | On-side | Dark | Table 14 |
| | 3 | 40 | 75 | On-side | Dark | Table 15 |

TABLE 2

Stability results on batch 1 stored at 25° C./40% RH/On-side/Dark (20 mL syringe, 10 mL fill volume)

| Test | Acceptance criteria | Sampling point (months) | | | | | | |
|---|---|---|---|---|---|---|---|---|
| | | 0 | 3 | 6 | 9 | 12 | 18 | 24 |
| Oxygen in headspace by GC-TCD | Report value, % | 16.6, 17.5, 16.5 | 19.1, 18.8, 19.1 | 20.0, 20.2, 19.9 | 19.9, 20.0, 20.1 | 20.1, 20.1, 20.2 | 20.1, 20.3, 19.9 | — |
| Free Gd by colour limit test | Not detected | ND | ND | ND | ND | ND | ND | — |

— Testing not required as 30° C./75% RH results cover this sampling point

TABLE 3

Stability results on batch 1 stored at 30° C./75% RH/On-side/Dark (20 mL syringe, 10 mL fill volume)

| Test | Acceptance criteria | Sampling point (months) | | | | | | |
|---|---|---|---|---|---|---|---|---|
| | | 0 | 3 | 6 | 9 | 12 | 18 | 24 |
| Oxygen in headspace by GC-TCD | Report value, % | 16.6, 17.5, 16.5 | 18.3, 18.0, 18.4 | 19.6, 19.8, 19.8 | 19.7, 19.6, 19.7 | 19.9, 20.3, 20.0 | 19.6, 19.7, 19.8 | 20.1, 20.2, 20.1 |
| Free Gd by colour limit test | Not detected | ND | ND | ND | ND | ND | ND | ND |

TABLE 4

Stability results on batch 1 stored at 40° C./20% RH/On-side/Dark (20 mL syringe, 10 mL fill volume)

| Test | Acceptance criteria | Sampling point (months) | | | |
|---|---|---|---|---|---|
| | | 0 | 1 | 3 | 6 |
| Oxygen in headspace by GC-TCD | Report value, % | 16.6, 17.5, 16.5 | 16.7, 16.3, 17.5 | 18.7, 17.8, 18.2 | 19.0, 19.5, 19.4 |
| Free Gd by colour limit test | Not detected | ND | ND | ND | ND |

TABLE 5

Stability results on batch 1 stored at 40° C./75% RH/On-side/Dark (20 mL syringe, 10 mL fill volume)

| Test | Acceptance criteria | Sampling point (months) | |
|---|---|---|---|
| | | 0 | 6 |
| Oxygen in headspace by GC-TCD | Report value, % | 16.6, 17.5, 16.5 | 19.0, 19.0, 18.7 |
| Free Gd by colour limit test | Not detected | | ND ND |

TABLE 6

Stability results on batch 1 stored at 25 °C./Ambient/On-side (20 mL syringe, 10 mL fill volume) Photo stability study

| Test | Acceptance criteria | Sampling point (days) | | | | Dark control |
|---|---|---|---|---|---|---|
| | | 0[1)] | 3[2)] | 7[3)] | 23[4)] | |
| Oxygen in headspace by GC-TCD | Report value, % | 18.3, 18.0, 18.4 | 18.6, 19.4, 18.7 | 19.0, 18.9, 19.0 | 16.0, 15.6, 15.8 | 19.9, 19.2, 19.8 |
| Free Gd by colour limit test | Not detected | ND | ND | ND | ND | ND |

— means that the test has not been performed at the specified sampling point,
ND: Not detected,
LT: Less than,
NLT: Not less than,
NMT: Not more than
[1)]Zero point photo stability: SN1506.013, data from 3 months sampling point
[2)]Lux: 0.358 mill lux h, UVA 30.5 Wh/m$^2$
[3)]Lux: 0.832 mill lux h, UVA 71 Wh/m$^2$
[4)]Lux: 1.64 mill lux h, UVA 206.1 Wh/m$^2$
5) Reported according to method at the time of testing

TABLE 7

Stability results on batch 2 stored at 25° C./40% RH/On-side/Dark (20 mL syringe, 15 mL fill volume)

| Test | Acceptance criteria | Sampling point (months) | | | | | | |
|---|---|---|---|---|---|---|---|---|
| | | 0 | 3 | 6 | 9 | 12 | 18 | 24 |
| Oxygen in headspace by GC-TCD | Report value, % | 15.9, 15.6, 16.4 | 19.8, 19.0, 19.1 | 20.1, 20.1, 19.8 | 20.2, 20.3, 20.1 | 20.1, 20.2, 20.2 | 20.6, 20.2, 20.1 | — |

TABLE 7-continued

Stability results on batch 2 stored at 25° C./40% RH/On-side/Dark (20 mL syringe, 15 mL fill volume)

| Test | Acceptance criteria | Sampling point (months) | | | | | |
|---|---|---|---|---|---|---|---|
| | | 0 | 3 | 6 | 9 | 12 | 18 | 24 |
| Free Gd by colour limit test | Not detected | ND | ND | ND | ND | ND | ND | — |

— Testing not required as 30° C./75% RH results cover this sampling point

TABLE 8

Stability results on batch 2 stored at 30° C./75% RH/On-side/Dark (20 mL syringe, 15 mL fill volume)

| Test | Acceptance criteria | Sampling point (months) | | | | | | |
|---|---|---|---|---|---|---|---|---|
| | | 0 | 3 | 6 | 9 | 12 | 18 | 24 |
| Oxygen in headspace by GC-TCD | Report value, % | 15.9, 15.6, 16.4 | 18.3, 18.1, 18.7 | 19.6, 19.8, 19.5 | 19.7, 19.6, 19.8 | 19.8, 19.9, 20.0 | 20.2, 20.2, 19.9 | 19.8, 20.3, 19.7 |
| Free Gd by colour limit test | Not detected | ND | ND | ND | ND | ND | ND | ND |

TABLE 9

Stability results on batch 2 stored at 40° C./20% RH/On-side/Dark (20 mL syringe, 15 mL fill volume)

| Test | Acceptance criteria | Sampling point (months) | | | |
|---|---|---|---|---|---|
| | | 0 | 1 | 3 | 6 |
| Oxygen in headspace by GC-TCD | Report value, % | 15.9, 15.6, 16.4 | 16.8, 17.1, 17.7 | 18.8, 18.2, 18.2 | 19.5, 19.4, 19.6 |
| Free Gd by colour limit test | Not detected | ND | ND | ND | ND |

TABLE 10

Stability results on batch 2 stored at 40° C./75% RH/On-side/Dark (20 mL syringe, 15 mL fill volume)

| Test | Acceptance criteria | Sampling point (months) | | |
|---|---|---|---|---|
| | | 0 | 3 | 6 |
| Oxygen in headspace by GC-TCD | Report value, % | 15.9, 15.6, 16.4 | 17.9, 17.8, 17.9 | 19.2, 19.4, 19.2 |
| Free Gd by colour limit test | Not detected | ND | ND | ND |

TABLE 11

Stability results on batch 1 stored at −20° C. to 60° C./Ambient/On-side/Dark (20 mL syringe, 10 mL fill volume). Temperature cycling study

| Test | Acceptance criteria | Sampling point (days) | |
|---|---|---|---|
| | | 0[1)] | 12 |
| Oxygen in headspace by GC-TCD | Report value, % | 18.3, 18.0, 18.4 | 17.1, 17.0, 17.3 |
| Free Gd by colour limit test | Not detected | ND | ND |

TABLE 12

Stability results on batch 12907764 stored at 25° C./40% RH/On-side/Dark (20 mL syringe, 20 mL fill volume)

| Test | Acceptance criteria | Sampling point (months) | | | | | | |
|---|---|---|---|---|---|---|---|---|
| | | 0 | 3 | 6 | 9 | 12 | 18 | 24 |
| Oxygen in headspace by GC-TCD | Report value, % | 12.7, 12.8, 13.5 | 19.3, 19.3, 19.1 | 19.5, 19.6, 19.5 | 19.9, 20.0, 20.0 | 20.1, 20.3, 20.2 | 20.3, 20.1, 20.4 | — |
| Free Gd by colour limit test | Not detected | ND | ND | ND | ND | ND | ND | — |

— Testing not required as 30° C./75% RH results cover this sampling point

TABLE 13

Stability results on batch 3 stored at 30° C./75% RH/On-side/Dark (20 mL syringe, 20 mL fill volume)

| Test | Acceptance criteria | Sampling point (months) | | | | | | |
|---|---|---|---|---|---|---|---|---|
| | | 0 | 3 | 6 | 9 | 12 | 18 | 24 |
| Oxygen in headspace by GC-TCD | Report value, % | 12.7, 12.8, 13.5 | 18.7, 18.5, 18.2 | 19.5, 19.6, 19.4 | 19.8, 19.7, 19.8 | 19.8, 20.1, 19.7 | 20.0, 19.9, 19.8 | 21.0, 21.0, 21.2 |
| Free Gd by colour limit test | Not detected | ND | ND | ND | ND | ND | ND | ND |

TABLE 14

Stability results on batch 3 stored at 40° C./20% RH/On-side/Dark (20 mL syringe, 20 mL fill volume)

| Test | Acceptance criteria | Sampling point (months) | | | |
|---|---|---|---|---|---|
| | | 0 | 1 | 3 | 6 |
| Oxygen in headspace by GC-TCD | Report value, % | 12.7, 12.8, 13.5 | 16.6, 17.1, 17.0 | 18.2, 18.1, 18.5 | 19.5, 19.8, 19.3 |
| Free Gd by colour limit test | Not detected | ND | ND | ND | ND |

TABLE 15

Stability results on batch 3 stored at 40° C./75% RH/On-side/Dark (20 mL syringe, 20 mL volume)

| Test | Acceptance criteria | Sampling point (months) 0 | Sampling point (months) 6 |
|---|---|---|---|
| Oxygen in headspace by GC-TCD | Report value, % | 12.7, 12.8, 13.5 | 19.4, 19.6, 19.5 |
| Free Gd by colour limit test | Not detected | ND | ND |

The invention claimed is:

1. A method for providing a gadolinium-DOTA solution wherein said method comprises:
   (i) manufacturing a batch of said gadolinium-DOTA solution; and,
   (ii) dispensing said gadolinium-DOTA solution into a pharmaceutical-grade cyclic olefin plastic container, wherein said container is a syringe;
   wherein said syringe comprises oxygen in the headspace of the syringe and is sufficiently transparent to permit visual verification of the contents of the syringe.

2. The method as defined in claim 1 wherein said gadolinium-DOTA is the meglumine salt of gadolinium-DOTA.

3. The method as defined in claim 1 wherein said gadolinium-DOTA solution further comprises a mol/mol amount of free DOTA between 0.002% and 0.4%.

4. The method as defined in claim 1 wherein said syringe has a 10 mL volume.

5. The method as defined in claim 1 wherein said syringe has a 15 mL volume.

6. The method as defined in claim 1 wherein said syringe has a 20 mL volume.

7. The method as defined in claim 1 wherein said batch is a 400-1400L batch.

8. The method as defined in claim 1 wherein said method further comprises the step (iii) of storing said solution dispensed into said plastic containers.

9. The method as defined in claim 8 wherein said storing is for more than 90 days.

10. The method as defined in claim 8 wherein said storing is for up to 30 months.

11. The method as defined in claim 8 wherein said storing is for up to 36 months.

12. The method as defined in claim 8 wherein said storing is at temperatures up to 30° C.

13. The method as defined in claim 1 wherein said dispensing includes an overfill.

14. The method as defined in claim 13 wherein said overfill is 1-5% of the final desired volume.

15. The method as defined in claim 1 wherein nitrogen is not used as an excipient in the plastic container headspace.

* * * * *